US005176707A

United States Patent [19]

Phillips

[11] Patent Number: 5,176,707

[45] Date of Patent: Jan. 5, 1993

[54] SPINAL ADJUSTMENT DEVICE

[76] Inventor: Edward A. Phillips, 3712 West Loma Ln., Phoenix, Ariz. 85051

[21] Appl. No.: 787,088

[22] Filed: Nov. 4, 1991

[51] Int. Cl.[5] .......... A61F 5/00

[52] U.S. Cl. .......... 606/241; 602/34

[58] Field of Search .......... 128/67-71, 128/75, 84 R, 84 C; 482/95, 96, 131, 143-145, 907; 602/32-36; 606/241, 242

[56] References Cited

U.S. PATENT DOCUMENTS 2,631,582 3/1953 Bensfield .
4,362,151 12/1982 Cottrell .
4,489,713 12/1984 Latensel .
4,531,514 7/1985 McDonald et al. .
4,580,554 4/1986 Goodley .
4,602,619 7/1986 Wolf et al. .
4,641,637 2/1987 Rosen .
5,010,880 4/1991 Lamb .
5,040,523 8/1991 Wu ..

FOREIGN PATENT DOCUMENTS 2524799 10/1983 France .
2524800 10/1983 France .

*Primary Examiner*—Robert Bahr
*Assistant Examiner*—Linda C. M. Dvorak
*Attorney, Agent, or Firm*—Rosenbaum & Schwartz

[57] ABSTRACT

A method and apparatus are presented in which a generally vertical force is applied to a person's lower spine in approximately a perpendicular direction to the axis of elongation of the spine. In particular, the person is placed on his back in a substantially supine position. A restraining belt is then placed about the person's pelvic area and a lifting force is applied in an upward direction. The person can then apply pressure to one of various footrests to adjust the amount and direction of the force applied to the spine for maximum relief from lower back discomfort. The method and apparatus may also be used to adjust other body areas, such as the shoulders or neck, by applying the belt to the pertinent body area.

5 Claims, 1 Drawing Sheet

FIG. 1
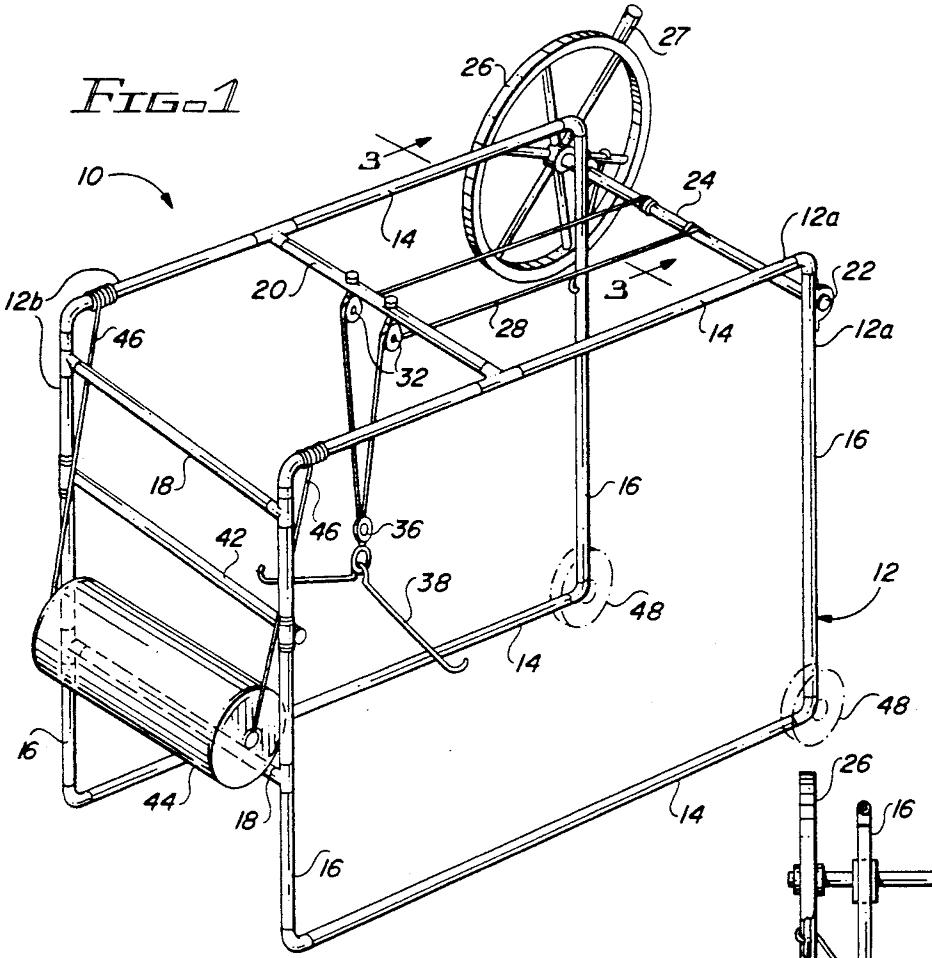
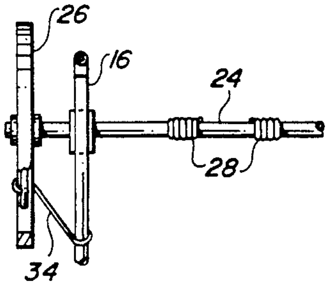
FIG. 3
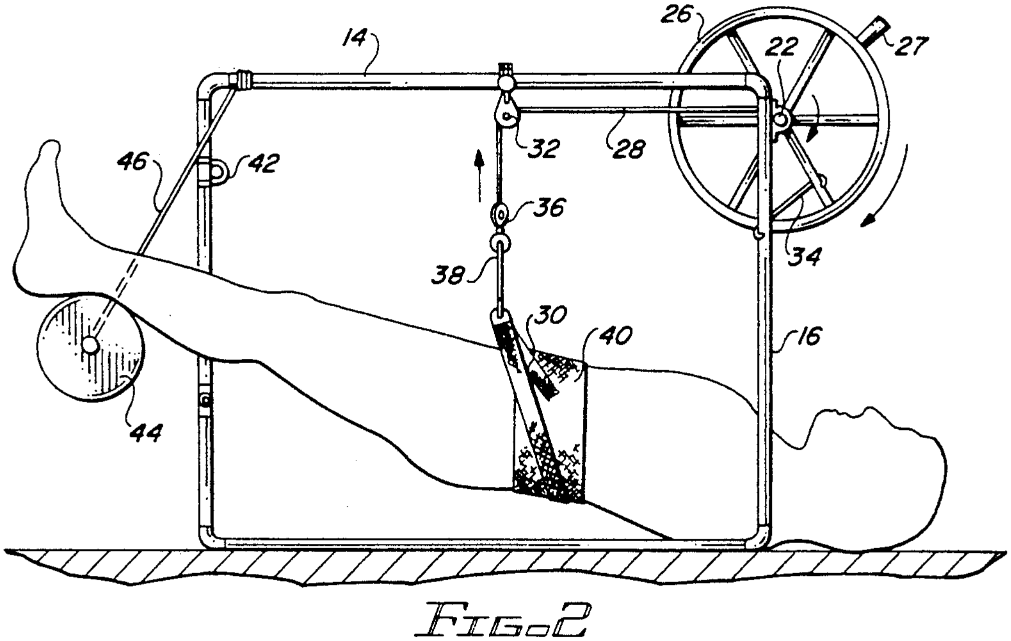
FIG. 2

SPINAL ADJUSTMENT DEVICE

BACKGROUND OF THE INVENTION

This invention relates in general to a method and apparatus for relieving bodily discomfort, and more particularly to a method and apparatus for applying pressure to various areas along the human spine to relieve back and neck pain.

Various forms of inventions for applying force to a person's spine to relieve back and neck discomfort have been designed. U.S. Pat. No. 3,800,787 describes a traction apparatus consisting of a bed with an overhead traction frame. A horizontal traction board for supporting the calves of the legs in a horizontal position above the bed is suspended by cables from the frame. U.S. Pat. No. 4,489,713 describes a traction invention having a bed with an overhead traction frame, from which is suspended a gear motor used to adjust the vertical position of a knee and ankle supporting mechanism, which thereby results in an applied force to a person's lower back U.S. Pat. No. 4,531,514 describes an orthopedic traction invention for providing traction and flexion to the lumbar spine through the use of a trapeze or T-bar, a double-pull pelvic traction belt, and hoisting means. U.S. Pat. No. 4,602,619 describes an invention in which alternate amounts of tractive force are applied to portions of the spine at an angle to the axis of elongation of the spine. U.S. Pat. Nos. 4,362,151, 4,489,713, 4,531,514, and 4,602,619 proVide a means for the user to adjust only the vertical positioning of the pelvic and buttocks area. There is no facility to allow the user to exert horizontal pressure on these areas.

SUMMARY OF THE INVENTION

It is an object of this invention to provide an improved traction device for treatment of spinal discomfort, in addition to a means for adjusting the vertical and horizontal positions of pressure applied to the pelvic and buttocks area. It is also an object of this invention to provide a means whereby a person can adjust the amount and direction of force applied to the lower spine through the application of pressure with his or her feet to various footrests on the invention.

Use of the present invention requires that a person be placed in a supine position on a surface beneath the device. A flexible, adjustable, restraining belt is then provided which encircles the person's pelvic and abdominal area. Straps that are fixed to the belt are then releasably attached to a connector which is in turn connected to flexible cable that passes along a line tracking means for support of the cable. The cable is attached at its opposite end to take-up means whereby the person can adjust the vertical position of the restraining belt and, thereby, can adjust the vertical height that the person's pelvic and abdominal area is elevated off of the surface beneath the invention.

By utilizing the restraining belt in this way, the person will experience force applied to the pelvic and abdominal area in a substantially perpendicular direction to the axis of elongation of the spine, similar to that provided by previous inventions. However, the present invention also provides the person who uses it with various footrests that can be used to adjust the amount and direction of the force exerted on the lower spine.

Various adjustable or fixed cross members are available so that the person can either rest his feet and ankles on them or apply pressure to them with the bottoms of his feet. Applying such pressure to the cross members with the bottoms of his feet allows the person to increase the force applied to the lower spine and change the direction of application of the force to a direction approaching that parallel to or co-planar with the axis of elongation of the spine.

Additionally, an adjustable cushioned footrest may be provided for the person to rest his feet and ankles on. The person can apply pressure to the cushioned footrest with the bottoms of his feet in much the same manner as with the rigid cross members. Such action achieves the same result of increasing the force applied to the lower spine and changing the direction of application to a direction approaching that parallel to the axis of elongation of the spine.

The objects and advantages of this invention will appear more fully from the following description made in conjunction with the accompanying drawings.

BRIEF DESCRIPTION OF THE DRAWINGS

FIG. 1 is a perspective view of an embodiment of the invention with retractable wheels shown in phantom.

FIG. 2 is a side elevational view illustrating an embodiment of the invention in use.

FIG. 3 is a partial elevational view of an embodiment of a flywheel and axle assembly of the invention.

DETAILED DESCRIPTION OF THE PREFERRED EMBODIMENT

Referring now in detail to the embodiment chosen for the purpose of illustration, the invention 10, as shown in FIG. 1, is comprised of a rigid tubular frame 12, constructed of material such as metal tube or channel, having main longitudinal members 14 and main vertical members 16. Co-planar sections 12*a* and 12*b* of rigid tubular frame 12 are connected by posterior cross members 18 and top cross member 20, both preferably constructed of material such as that of the frame. The frame may be of any suitable shape, such as an "A" or "bow" shaped frame, and may be of any suitable material, such as aluminum, galvanized steel, or rigid plastic.

Toward the top and anterior portion of the rigid tubular frame 12, and attached to the main vertical members 16 by axle bearings 22, there is an axle 24 with a means for rotating the axle, such as adjustable flywheel 26 and flywheel handle 27, attached to one end. The means for rotating the axle may be a spoked or solid flywheel, a ratchet-type device, or any other suitable take-up means. Attached to the midsection of the axle 24 are one or more lengths of flexible wire cable or cord line, such as support cable 28, that wind around the axle 24 when adjustment flywheel 26 is turned.

As shown in FIG. 2, the adjustment flywheel 26 is turned to adjust the vertical position of a flexible restraint, such as support belt 30, through a line tracking means, such as support pulleys 32. The position of adjustment flywheel 26 is secured with a locking mechanism, such as flywheel positioning key 34. A ratchet-type take-up means would require no such locking mechanism. The support cable 28 runs from the midsection of the axle 24 through the line tracking means, such as one or more support pulleys 32, which are attached to the underside of top cross member 20, and down to a connector, such as support ring and pulley assembly 36, to which said cable is attached. Where only one pulley 32 is used, assembly 36 consists only of a support ring. A rigid support member 38 is connected to said support cable 28 through the connector, such as support ring and pulley assembly 36, and is connected at both ends to support belt 40.

At the posterior end of the invention 10 are one or more adjustable footrests, such as vertically adjustable cross member 42 and cushioned footrest 44, as shown in FIG. 1. Said cushioned footrest 44 is connected to the posterior end of the upper main longitudinal members 14 with support cable 46. Said adjustable cross member 42 is connected through clamping means in the upper area of posterior main vertical members 16.

The adjustable cross member 42 and the cushioned footrest 44 are members on which pressure can be applied by a person with his feet in both horizontal and vertical directions, depending on the desired direction of pressure to be exerted on the person's spine.

Retractable wheels 48 may be added to the bottom corners of rigid tubular frame 12 to provide means for moving the device.

While the invention has been described with reference to the preferred embodiments thereof, those skilled in the art will understand that variations in design, detail, size, shape, and choice of materials for manufacture may be made and still fall within the spirit and scope of the present invention, which is intended to be limited only by the claims appended hereto.

What is claimed is:

1. An apparatus for relieving a person's skeletal discomfort, said apparatus comprising:

a rigid frame member of sufficient stability and strength so as to support substantially all of the person's weight while using said apparatus;

line tracking means fixably mounted to said frame member for vertically positioning the person's skeletal area over a support surface beneath said apparatus, said line tracking means comprising:

(a) a rigid take-up member rotatably mounted near a top first end of said frame member;

(b) locking means for securing an angular position of said take-up member, said locking means being of sufficient strength to withstand the gravitational force exerted by a person mounted in said apparatus;

(c) at least one line tracking guide connected to said frame member such that flexible support cables strewn through said line tracking means will hang vertically from, and substantially perpendicular to a top central portion of, said frame member; and (d) at least one flexible support cable fixably attached at its first end to said rigid take-up member and running from said rigid take-up member through said line tracking means, said flexible support cable being fixably attached at its second end to a restraint connector hanging vertically below at least one top centrally located cable guide and substantially beneath the top central portion of said frame member;

a rigid restraint support member suspended from said restraint connector;

a flexible restraint suspended from said rigid restraint support member, said restraint being used to mount the person in said apparatus; and at least one rigid footrest adjustably attached to a second end of said frame member.

2. The apparatus of claim 1 further comprising at least one moveable footrest adjustably attached to the second end of said frame member.

3. An apparatus for relieving a person's skeletal discomfort, said apparatus comprising:

a co-planar rigid tubular frame of at least two sections connected by a plurality of cross members fixably attached at each end to said co-planar rigid tubular frame;

line tracking means for vertical positioning of the person's body, said line tracking means comprising:

(a) an axle located near a top first end of said co-planar rigid tubular frame, said axle being rotatably connected to said co-planar rigid tubular frame through axle bearings;

(b) rotating means, fixably connected to at least one end of said axle, for rotation of said axle;

(c) locking means for securing an angular position of said rotating means and said axle;

(d) at least one pulley connected to at least one of said cross members located substantially near a top central position of said co-planar rigid tubular frame; and (e) at least one flexible support cable fixably attached at one end to said axle and running from said axle through said pulleys, said cable being fixably attached at its second end to a support mechanism hanging vertically below the top central portion of said co-planar rigid tubular frame;

a rigid support member suspended from said support mechanism;

a flexible support belt suspended from said rigid support member, said flexible support belt being used to mount the person in the device; and at least one rigid foot rest adjustably attached through clamping means to a second end of said co-planar rigid tubular frame.

4. The apparatus of claim 3 further comprising at least one moveable footrest adjustably attached through flexible cable to a top second end of said co-planar rigid tubular frame.

5. A method for relieving a peson's skeletal discomfort which comprises:

mounting the person's body in a flexible restraint that hangs from a rigid frame;

applying pressure to the person's skeletal area by elevating the person's restrained skeletal area above a support surface;

adjusting the vertical position of the person's skeletal area with respect to the support surface;

positioning the person's head and shoulders area so that they are in contact with the support surface; and applying pressure to a footrest with the person's feet simultaneously with said step of applying pressure to the person's skeletal area by elevating the person's restrained skeletal area above a support surface, thereby providing a horizontal force to the person's skeletal area parallel with the axis of elongation of the person's spine at the same time a vertical force is applied to the person's spine.

* * * * *